United States Patent
Hiyama et al.

(10) Patent No.: US 7,829,106 B2
(45) Date of Patent: Nov. 9, 2010

(54) COSMETIC COMPOSITION AND COSMETIC

(75) Inventors: Shinichiro Hiyama, Yokkaichi (JP); Yoshihiko Takase, Yokkaichi (JP); Shuji Hibino, Kusatsu (JP)

(73) Assignee: Taiyo Kagaku Co., Ltd., Yokkaichi-Shi (JP)

( * ) Notice: Subject to any disclaimer, the term of this patent is extended or adjusted under 35 U.S.C. 154(b) by 342 days.

(21) Appl. No.: 11/922,016

(22) PCT Filed: Jun. 12, 2006

(86) PCT No.: PCT/JP2006/311781
§ 371 (c)(1),
(2), (4) Date: Dec. 12, 2007

(87) PCT Pub. No.: WO2006/134886
PCT Pub. Date: Dec. 21, 2006

(65) Prior Publication Data
US 2009/0281199 A1  Nov. 12, 2009

(30) Foreign Application Priority Data
Jun. 13, 2005   (JP)   ............................. 2005-173032

(51) Int. Cl.
*A61K 9/00* (2006.01)
*A23D 9/00* (2006.01)

(52) U.S. Cl. ...................... 424/400; 554/227

(58) Field of Classification Search .................. None
See application file for complete search history.

(56) References Cited

U.S. PATENT DOCUMENTS

| | | | | |
|---|---|---|---|---|
| 3,959,491 A | * | 5/1976 | Young et al. | 514/775 |
| 4,857,321 A | * | 8/1989 | Thomas | 424/525 |
| 7,629,479 B2 | | 12/2009 | Kondo et al. | |

FOREIGN PATENT DOCUMENTS

| | | |
|---|---|---|
| EP | 1623694 A1 | 2/2006 |
| JP | 4-5213 A | 1/1992 |
| JP | 6-99275 A | 4/1994 |
| JP | 7-100355 A | 4/1995 |
| JP | 8-143420 A | 6/1996 |
| JP | 9-188754 A | 7/1997 |
| JP | 10-095749 A | 4/1998 |
| JP | 2001-064236 A | 3/2001 |
| JP | 2004-035420 A | 2/2004 |
| JP | 2004-256514 A | 9/2004 |
| WO | WO-2004/098544 A | 11/2004 |
| WO | WO-2005/051334 A1 | 6/2005 |
| WO | WO-2006/041011 A1 | 4/2006 |

* cited by examiner

*Primary Examiner*—Yvonne L Eyler
*Assistant Examiner*—Jennifer A Berrios
(74) *Attorney, Agent, or Firm*—Birch, Stewart, Kolasch & Birch, LLP.

(57) ABSTRACT

Among cleansing cosmetics for the purpose of removing makeup, the aqueous type cleansing cosmetics containing no oil at all or a small amount of oil have had a disadvantage that remover capability is weak even though they give reduced oily feel after cleansing. The liquid oil-based makeup remover has a low viscosity so that there has been a disadvantage in usefulness that the liquid oil-based makeup remover drips off upon taking on hand. An object of the present invention is to provide a composition for cosmetics which is excellent in usefulness, has excellent affinity to makeup soil, quickly suspends soil, and is excellent in stability and rinsability.

A composition for cosmetics is characterized in that the composition for cosmetics comprises a polyglycerol fatty acid ester obtained from a polyglycerol having a hydroxyl value of 1200 or less and primary hydroxyl groups in an amount of 50% or more of the total hydroxyl groups and one or more kinds of fatty acids having 8 to 22 carbon atoms, is excellent in stability, and has a viscosity of from 100 to 5000 mPa·s at 25° C., and whereby the above-mentioned problems are solved.

9 Claims, No Drawings

COSMETIC COMPOSITION AND COSMETIC

TECHNICAL FIELD

The present invention relates to a composition for cosmetics comprising a polyglycerol fatty acid ester obtained from a polyglycerol having a hydroxyl value of 1200 or less and primary hydroxyl groups in an amount of 50% or more of the total hydroxyl groups and one or more kinds of fatty acids having 8 to 22 carbon atoms. More specifically, the present invention relates to a composition for cosmetics which can be utilized in cleansing cosmetics.

BACKGROUND ART

In the field of cosmetics, cleansing cosmetics for the purpose of removing makeup are in the form of cream, milky lotion, or liquid. Also, the cleansing cosmetics are classified by types into emulsion type, oil type and aqueous type, and have been utilized depending upon their respective uses. However, the aqueous type cleansing cosmetics containing no oil at all or a small amount of oil have had a disadvantage that remover capability is weak even though they give reduced oily feel after cleansing. In addition, a cleansing cream and an oil gel that are water-in-oil emulsions have a continuous phase of oil, thereby having excellent affinity to makeup and excellent remover capability. However, the cleansing cream and the oil gel cannot be washed off with water so that there has been a disadvantage in usefulness. Therefore, in recent years, the mainstream of the cleansing cosmetics have been a liquid oil-based makeup remover which has excellent affinity to makeup soil and can be easily washed off with water. (for example, see Patent Publication 1) The liquid oil-based makeup remover is a self-emulsifiable oily liquid composition comprising a mixed system of an oily component and a surfactant. However, the liquid oil-based makeup remover has a low viscosity so that there has been a disadvantage in usefulness that the liquid oil-based makeup remover drips off upon taking on hand. On the other hand, there have been published techniques of a cleansing gel comprising a nonion activator, a sucrose fatty acid ester, a polyhydric alcohol, oil, water, or the like (for example, see Patent Publications 2 and 3). However, these techniques require the cleansing gel to contain various and large amounts of surfactants or contain a polyoxyethylene-based surfactant so that there has been a disadvantage in the aspect of safety.

Patent Publication 1: Japanese Examined Patent Publication No. Hei 6-99275

Patent Publication 2: Japanese Patent Laid-Open No. Hei 4-5213

Patent Publication 3: Japanese Patent Laid-Open No. Hei 8-143420

DISCLOSURE OF INVENTION

Problems to be Solved by the Invention

A problem to be solved by the present invention is to provide a composition for cosmetics which is excellent in usefulness, is more likely to have excellent affinity to makeup soil, quickly suspends soil, and is excellent in stability and rinsability.

Means to Solve the Problems

The present inventors have found that a specified polyglycerol fatty acid ester is used, thereby providing a composition to which a proper viscosity is given, and whereby the composition can be utilized for cleansing cosmetics or the like which is excellent in usefulness, is more likely to have excellent affinity to makeup soil, quickly suspends soil, and is excellent in stability and rinsability.

Specifically, the present invention relates to a composition for cosmetics characterized in that the composition for cosmetics comprises a polyglycerol fatty acid ester obtained from a polyglycerol having a hydroxyl value of 1200 or less and primary hydroxyl groups in an amount of 50% or more of the total hydroxyl groups and one or more kinds of fatty acids having 8 to 22 carbon atoms, and has a viscosity of from 100 to 5000 mPa·s at 25° C. More specifically, the present invention relates to a composition for cosmetics which can be utilized in cleansing cosmetics.

Effects of the Invention

The composition for cosmetics of the present invention characterized in that the composition for cosmetics comprises a polyglycerol fatty acid ester obtained from a polyglycerol having a hydroxyl value of 1200 or less and primary hydroxyl groups in an amount of 50% or more of the total hydroxyl groups and one or more kinds of fatty acids having 8 to 22 carbon atoms, and has a viscosity of from 100 to 5000 mPa·s at 25° C. is excellent in usefulness, remover capability, and rinsability, and can be utilized for cleansing cosmetics, emulsion cosmetics, and the like.

BEST MODE FOR CARRYING OUT THE INVENTION

A polyglycerol fatty acid ester used in the present invention is an ester of a linear or branched, saturated or unsaturated fatty acid having 8 to 22 carbon atoms, preferably 10 to 18 carbon atoms, and further preferably 14 to 18 carbon atoms, and a polyglycerol having a hydroxyl value of 1200 or less and primary hydroxyl groups in an amount of 50% or more of the total hydroxyl groups. The polyglycerol used in the present invention is a polyglycerol, wherein the polyglycerol has primary hydroxyl groups in an amount of 50% or more of the total hydroxyl groups in the polyglycerol. The polyglycerol has primary hydroxyl groups in an amount of preferably 55% or more, and more preferably 60% or more, from the viewpoint of further improving solubilization property and emulsion stability of the resulting polyglycerol fatty acid ester. In addition, the polyglycerol has primary hydroxyl groups in an amount of preferably 90% or less, from the viewpoint of productivity. Further, a polyglycerol has a hydroxyl value of 1200 or less, and one having a hydroxyl value of 1100 or less is more preferable, and one having a hydroxyl value of 1000 or less is even more preferable, from the viewpoint of easiness in adjusting HLB of a polyglycerol fatty acid ester in accordance with its applications. In addition, the polyglycerol having a hydroxyl value of 770 or more is preferable, from the viewpoint of operability and easiness in esterifying with a fatty acid. A ratio of primary hydroxyl groups to the total hydroxyl groups can be determined by a method for determining a nuclear magnetic resonance spectrum (NMR) with respect to carbon atoms. In addition, the hydroxyl value can be determined by a method known in the art. Here, a nuclear magnetic resonance spectrum (NMR) with respect to carbon atoms can be determined as follows. Five-hundred milligrams of a polyglycerol is dissolved in 2.8 ml of heavy water, and the solution is filtrated. Thereafter, 13CNMR (125 MHz) spectrum is obtained by gated decoupling. A peak intensity is proportional to the number of carbon atoms measured by gated decoupling technique. The 13C chemical shifts showing the presence of primary hydroxyl groups and secondary hydroxyl groups appears near 63 ppm for a methylene carbon (CH2OH) and near 71 ppm for a methyne carbon (CHOH), respectively. Abundance ratios of primary hydroxyl groups and secondary hydroxyl groups are calculated by the analysis of signal intensities of each of two kinds. However, the methyne carbon (CHOH) showing a secondary hydroxyl group overlaps with a peak of a methylene carbon further adjoining a methyne carbon bound to the methylene carbon showing a primary hydroxyl group, so that an integration value of the methyne carbon itself cannot be obtained. Therefore, the integration value is calculated by a signal intensity near 74 ppm of a methylene carbon (CH2) adjoining the methyne carbon (CHOH).

One or more kinds of the polyglycerol fatty acid esters obtained as mentioned above can be used, and the polyglycerol fatty acid ester has an HLB of preferably from 6 to 12 and the polyglycerol fatty acid ester has an HLB of further preferably from 8 to 12. Here, in a case where two or more kinds of the polyglycerol fatty acid esters are used, an HLB means an average HLB. Therefore, as an individual polyglycerol fatty acid ester, even though an HLB is outside the range of from 6 to 12, when an average HLB is in the range of from 6 to 12 using in combination of two or more kinds of the polyglycerol fatty acid esters, the polyglycerol fatty acid esters are included in the present invention. The polyglycerol fatty acid ester is contained in an amount of preferably from 3.5 to 30% by weight, more preferably from 5.0 to 25% by weight, and even more preferably from 7.0 to 25% by weight, in the composition of the present invention. In addition, when the amount is shown as relative to other components set forth below, the polyglycerol fatty acid ester is contained in an amount of preferably from 5 to 30 parts by weight, more preferably from 7 to 25 parts by weight, and even more preferably from 10 to 25 parts by weight. Here, the HLB refers to a balance of hydrophilicity and lipophilicity, and the calculation method of Griffin was used in the present invention.

$$HLB=20(1-S/A)$$

S: a saponification value of the polyglycerol fatty acid ester
A: a neutralization value of the raw material fatty acid In addition, the composition for cosmetics according to the present invention can contain also other surfactant such as a nonionic surfactant and an anionic surfactant, as long as the effects of the present invention are not impaired.

The polyhydric alcohol usable in the present invention includes one or more kinds of propylene glycol, glycerol, diglycerol, 1,3-butylene glycol, isoprene glycol, dipropylene glycol, polyethylene glycol, pentaerythritol, neopentyl glycol, sorbitol, sorbitan, maltitol, trehalose, and the like, and is preferably glycerol, 1,3-butylene glycol, propylene glycol, sorbitol, or maltitol. The polyhydric alcohol is contained in an amount of from 5 to 30 parts by weight, and preferably in an amount of from 10 to 20 parts by weight, in the composition of the present invention.

An oily component usable in the present invention usually comprises an oily component showing a liquid and/or pasty state at room temperature that can be utilized for cosmetics (room temperature herein refers to a range of from 15° to 25° C.) as a main component. The oil component is exemplified by natural animal or plant fats and oils and semi-synthesized fats and oils, hydrocarbon oils, higher fatty acids, ester oils, glyceride oils, silicone oils, components of purified oils from animals and plants or synthetic oils, fat-soluble vitamins, and the like.

The specific natural animal or plant fats and oils and semi-synthesized fats and oils include avocado oil, linseed oil, almond oil, olive oil, wheat germ oil, sesame oil, rice germ oil, rice bran oil, safflower oil, soybean oil, evening primrose oil, Indian corn oil, rapeseed oil, horse fat, palm oil, palm kernel oil, castor oil, sunflower oil, jojoba oil, macadamia nut oil, coconut oil, hardened coconut oil, peanut oil, lanolin and the like.

The hydrocarbon oil includes squalane, squalene, liquid paraffin, Vaseline, and the like. The ester oil includes diisobutyl adipate, 2-hexyldecyl adipate, di-2-heptylundecyl adipate, isostearyl isostearate, trimethylolpropane triisostearate, cetyl 2-ethylhexanoate, neopentyl glycol di-2-ethylhexanoate, trimethylolpropane tri-2-ethylhexanoate, pentaerythritol tetra-2-ethylhexanoate, cetyl octanoate, oleyl oleate, octyl dodecyl oleate, decyl oleate, neopentyl glycol dicaprate, 2-ethylhexyl succinate, isocetyl stearate, butyl stearate, diisopropyl sebacate, cetyl lactate, tetradecyl lactate, 2-ethylhexyl palmitate, 2-hexyldecyl palmitate, 2-heptylundecyl palmitate, cholesteryl 12-hydroxystearate, phytostearyl oleate, diisostearyl malate, paramethoxycinnamic acid ester, pentaerythritol tetrarosinate, and the like.

The glyceride oil includes glyceryl triisostearate, glyceryl triisopalmitate, glyceryl tri-2-ethylhexanoate, glyceryl tritetradecanoate, glyceryl diparamethoxycinnamate monoisoocylate, and the like. The silicone oil includes higher alkoxy-modified silicones, alkyl-modified silicones and higher fatty acid ester-modified silicones such as dimethyl polysiloxane, methylphenyl polysiloxane, methyl hydrogen polysiloxane, octamethyl cyclopentanesiloxane, decamethyl cyclohexasiloxane, and stearoxy silicone, and the like. The fat-soluble vitamin includes tocopherol or a derivative thereof, retinol or a derivative thereof, and the like.

The oily component used in the present invention is not limited to the specific examples described as the above. In addition, even an oily component showing a solid state can be contained in an amount that has no effect to maintain a liquid state. The oily component of the present invention is used in admixture of one or more kinds. The oily component is contained in an amount of from 40 to 90 parts by weight, and preferably from 40 to 80 parts by weight, in the composition of the present invention.

The composition for cosmetics of the present invention can be easily obtained by adding and mixing water to the above-mentioned components while stirring, or combining all the above-mentioned essential components and water and thereafter mixing the mixture. The water content of the present invention is properly selected by other components and the contents thereof. The water is usually contained in an amount of from 0.1 to 20 parts by weight, and preferably from 0.5 to 20 parts by weight. The composition for cosmetics of the present invention has a viscosity of from 100 to 5000 mPa·s at 25° C., and preferably a viscosity of from 200 to 1000 mPa·s at 25° C. In the case of a viscosity of lower than 100 mPa·s, there is a disadvantage in usefulness that the composition is likely to drip off from hand. In the case of a viscosity of more than 5000 mPa·s, it is more difficult to pull out from a pump container. The viscosity of the composition for cosmetics of the present invention can be determined with a B-type viscometer.

A lamellar liquid crystal structure in the present invention refers to a structure in a state which preserves its fluidity while retaining regularity of a molecular arrangement in which a bilayer membrane of an amphiphilic molecule and water are alternately oriented. The lamellar liquid crystal structure shows a peculiar optical characteristic, which is optical anisotropy, that can be confirmed by observation with a polarizing plate and a polarizing microscope. In addition, a structure called flow birefringence, which normally does not have an optical characteristic but in which the optical characteristic can be confirmed by observation with a polarizing plate by applying a stress to the substance, is also included in the lamellar liquid crystal structure of the present invention.

The present invention can properly contain lower alcohols, a powder, functional beads, capsules, an antioxidant, an ultraviolet absorbent, a plant extract, a moisturizing agent, a bactericidal agent, an anti-inflammatory agent, a preservative, a pigment, a perfume or the like which are usually used, in addition to the above-mentioned components. The above-mentioned components (the polyglycerol fatty acid ester, the polyhydric alcohol, the oily component, water) are totally contained in an amount of preferably 70% by weight or more, and further preferably 80% by weight or more.

The composition for cosmetics of the present invention obtained as mentioned above can be utilized for cleansing cosmetics, emulsion cosmetics, and the like. Preferably, the composition is utilized for cleansing cosmetics.

The present invention will be explained hereinbelow by means of specific Examples, without intending to limit the present invention thereto.

EXAMPLES

Cleansing cosmetics were prepared according to the formulation compositions of Examples 1 to 15 and Comparative Examples 1 to 11 as shown in the following table and evaluated based on the following Evaluation Criteria. The results are shown in Tables 1 to 4.

(Evaluation Method and Evaluation Criteria)

The following evaluations are the averages of the evaluations of 20 panelists.

All components shown in Tables 1 to 4 were mixed, and heated to dissolve and mixed with an anchor mixer at 80° C. or more. The mixtures were cooled to 35° C. or less while stirring with an anchor mixer, to give compositions for cosmetics.

1) Appearance Property

Appearance of the prepared composition was visually evaluated.

2) Spread

The prepared composition was taken on the back of hand and the sensory evaluation was made.

Evaluation
⊚: Very good
○: Good
Δ: Normal
x: Poor
Please note, however, that the separated composition was not determined and was defined as avaluative.

3) Viscosity

The prepared composition was determined with a B-type viscometer at 25° C. Please note, however, that the separated composition was not determined and the evaluation was made as x.

4) Remover Capability

About 0.5 g of the prepared composition was taken on hands. The extent of removal of lipstick soil after massages for 10 times was visually evaluated.

Evaluation
⊚: Completely removed
○: Mostly removed
Δ: Slightly remains
x: Hardly removed
Please note, however, that the separated composition was not determined and was defined as avaluative.

5) Refreshing Feel After Cleansing

Each of the compositions prepared by Examples and Comparative Examples was taken on the back of hand and the sensory evaluation was made on feel to the skin after evaluating remover capability.
⊚: Very refleshing
○: Refleshing
Δ: Slightly slimy
x: Slimy
Please note, however, that the separated composition was not determined and was defined as avaluative.

6) Formation of Lamellar Liquid Crystal

The prepared composition was observed for the formation of a lamellar liquid crystal by a polarizing microscope.

7) Stability

The prepared composition was stored at a low temperature (5° C.) for 1 month, and the state of the composition was observed.
○: Stable;
Δ: Not separated but slightly cloudy
x: Separated

TABLE 1

| | Example (% by weight) | | | | | | |
|---|---|---|---|---|---|---|---|
| Component | 1 | 2 | 3 | 4 | 5 | 6 | 7 |
| Water | 8.0 | 8.0 | 8.0 | 8.0 | 8.0 | 8.0 | 8.0 |
| Maltitol | 17.0 | 17.0 | 17.0 | 17.0 | 17.0 | 17.0 | 17.0 |
| Octyl Palmitate | 69.0 | 67.0 | 60.0 | | 60.0 | 47.0 | 60.0 |
| Liquid Paraffin | | | | 60.0 | | | |
| Polyglyceryl Dioleate Polyglycerol Hydroxyl Value of 871 Primary Hydroxyl Groups of 70.5% HLB of 11.9 | 6.0 | 8.0 | 15.0 | 15.0 | | 28.0 | 15.0 |
| Polyglyceryl Diisostearate Polyglycerol Hydroxyl Value of 871 Primary Hydroxyl Groups of 70.5% HLB of 10.1 | | | | | 15.0 | | |
| Appearance Property (25° C.) | Semi-transparent | Transparent | Transparent | Transparent | Transparent | Transparent | Semi-transparent |
| Spread | ⊚ | ⊚ | ⊚ | ⊚ | ⊚ | ○ | ⊚ |

TABLE 1-continued

| Component | Example (% by weight) | | | | | | |
|---|---|---|---|---|---|---|---|
| | 1 | 2 | 3 | 4 | 5 | 6 | 7 |
| Viscosity (25° C., mPa · s) | 300 | 450 | 650 | 1000 | 900 | 1800 | 400 |
| Remover Capability | ◉ | ◉ | ◉ | ◉ | ◉ | ◉ | ◉ |
| Refreshing Feel After Cleansing | ○ | ○ | ◉ | ◉ | ◉ | ◉ | ◉ |
| Formation of Lamellar Liquid Crystal | Formed | Formed | Formed | Formed | Formed | Formed | Formed |
| Stability | ○ | ○ | ○ | ○ | ○ | ○ | ○ |

TABLE 2

| Component | Example (% by weight) | | | | | | | |
|---|---|---|---|---|---|---|---|---|
| | 8 | 9 | 10 | 11 | 12 | 13 | 14 | 15 |
| Water | 8.0 | 8.0 | 8.0 | 5.0 | 8.0 | 1.0 | 0.3 | 8.0 |
| Maltitol | 17.0 | 17.0 | 17.0 | 25.0 | 17.0 | 4.0 | 19.7 | 17.0 |
| Octyl Palmitate | 60.0 | 60.0 | 60.0 | 33.0 | 60.0 | 85.0 | 65.0 | 60.0 |
| Liquid Paraffin | | | | 22.0 | | | | |
| Polyglyceryl Tetraoleate Polyglycerol Hydroxyl Value of 871 Primary Hydroxyl Groups of 70.5% HLB of 7.0 | | | | | 15.0 | | | |
| Polyglyceryl Dioleate Polyglycerol Hydroxyl Value of 871 Primary Hydroxyl Groups of 70.5% HLB of 11.9 | 10.0 | 10.0 | 10.0 | 15.0 | | 10.0 | 15.0 | |
| Polyglyceryl Dimyristate Polyglycerol Hydroxyl Value of 871 Primary Hydroxyl Groups of 70.5% HLB of 12.0 | | | | | | | | 15.0 |
| Polyglyceryl Dioleate Polyglycerol Hydroxyl Value of 871 Primary Hydroxyl Groups of 39.6% HLB of 11.9 | 5.0 | | | | | | | |
| Polyglyceryl Dimyristate Polyglycerol Hydroxyl Value of 877 Primary Hydroxyl Groups of 39.6% HLB of 12.0 | | | | 5.0 | | | | |
| Polyglyceryl Tetraoleate Polyglycerol Hydroxyl Value of 871 Primary Hydroxyl Groups of 39.6% HLB of 7.0 | | 5.0 | | | | | | |
| Appearance Property (25° C.) | Transparent | Transparent | Transparent | Transparent | Transparent | Transparent | Semi-transparent | Transparent |
| Spread | ○ | ○ | ○ | ○ | ○ | ◉ | ○ | ○ |
| Viscosity (25° C., mPa · s) | 950 | 850 | 1100 | 1500 | 650 | 150 | 2000 | 1300 |
| Remover Capability | ◉ | ◉ | ◉ | ◉ | ◉ | ◉ | ◉ | ◉ |
| Refreshing Feel After Cleansing | ◉ | ○ | ◉ | ◉ | ○ | ○ | ○ | ◉ |
| Formation of Lamellar Liquid Crystal | Formed | Formed | Formed | Formed | Formed | Formed | Formed | Formed |
| Stability | ○ | ○ | ○ | ○ | ○ | ○ | ○ | ○ |

TABLE 3

| Component | Comparative Example (% by weight) | | | | | | |
|---|---|---|---|---|---|---|---|
| | 1 | 2 | 3 | 4 | 5 | 6 | 7 |
| Water | 8.0 | 8.0 | 8.0 | 8.0 | 8.0 | 8.0 | 11.0 |
| Maltitol | 17.0 | 17.0 | 17.0 | 17.0 | 3.0 | 35.0 | 29.0 |
| Octyl Palmitate | 60.0 | 60.0 | 72.0 | 40.0 | 74.0 | 42.0 | 35.0 |
| Polyglyceryl Dioleate | | | 3.0 | 35.0 | 15.0 | 15.0 | 25.0 |

TABLE 3-continued

| | Comparative Example (% by weight) | | | | | | |
|---|---|---|---|---|---|---|---|
| Component | 1 | 2 | 3 | 4 | 5 | 6 | 7 |
| Polyglycerol Hydroxyl Value of 871 Primary Hydroxyl Groups of 70.5% HLB of 11.9 | | | | | | | |
| Polyglyceryl Triisostearate Polyglycerol Hydroxyl Value of 871 Primary Hydroxyl Groups of 70.5% HLB of 5.0 | 15.0 | | | | | | |
| Polyglyceryl Monooleate Polyglycerol Hydroxyl Value of 871 Primary Hydroxyl Groups of 70.5% HLB of 15.0 | | 15.0 | | | | | |
| Appearance Property (25° C.) | Separated | Separated | Separated | Transparent | Separated | Transparent | Transparent |
| Spread | Avaluative | Avaluative | Avaluative | X | Avaluative | ○ | X |
| Viscosity (25° C., mPa · s) | X | X | X | 6800 | X | 50 or less | 5900 |
| Remover Capability | Avaluative | Avaluative | Avaluative | ○ | Avaluative | Δ | Δ |
| Refreshing Feel After Cleansing | Avaluative | Avaluative | Avaluative | ○ | Avaluative | Δ | Δ |
| Formation of Lamellar Liquid Crystal | None | Formed | None | Formed | None | None | Formed |
| Stability | X | X | X | ○ | X | X | Δ |

TABLE 4

| | Comparative Example 2 (% by weight) | | | |
|---|---|---|---|---|
| Component | 8 | 9 | 10 | 11 |
| Water | | 25.0 | 8.0 | 8.0 |
| Maltitol | 17.0 | 17.0 | 17.0 | 17.0 |
| Octyl Palmitate | 68.0 | 43.0 | 60.0 | 60.0 |
| Polyglyceryl Dioleate Polyglycerol Hydroxyl Value of 871 Primary Hydroxyl Groups of 70.5% HLB of 11.9 | 15.0 | 15.0 | | |
| Polyglyceryl Dimyristate Polyglycerol Hydroxyl Value of 877 Primary Hydroxyl Groups of 39.6% HLB of 12.0 | | | 15.0 | |
| Diglyceryl Monooleate Polyglycerol Hydroxyl Value of 1352 Primary Hydroxyl Groups of 48.5% HLB of 7.0 | | | | 15.0 |
| Appearance Property (25° C.) | Separated | Separated | Transparent | Separated |
| Spread | Avaluative | Avaluative | ⊚ | Avaluative |
| Viscosity (25° C., mPa · s) | X | X | 450 | X |
| Remover Capability | Avaluative | Avaluative | ⊚ | Avaluative |
| Refreshing Feel After Cleansing | Avaluative | Avaluative | ○ | Avaluative |
| Formation of Lamellar Liquid Crystal | Formed | None | Formed | None |
| Stability | X | X | Δ | X |

INDUSTRIAL APPLICABILITY

As is clear from the Examples, the composition for cosmetics of the present invention has transparency, excellent in stability, has an excellent usefulness upon application and upon cleansing, and excellent in remover capability and rinsability. The composition is suitable for cleansing cosmetics.

The invention claimed is:
1. A composition for cosmetics, wherein said composition for cosmetics comprises a polyglycerol fatty acid ester obtained from a polyglycerol having a hydroxyl value of 1200 or less and primary hydroxyl groups in an amount of 50% or more and 70.5% or less of the total hydroxyl groups and one or more kinds of fatty acids having 8 to 22 carbon atoms, and has a viscosity of from 100 to 5000 mPa·s at 25° C.

2. The composition for cosmetics according to claim 1, wherein said composition for cosmetics comprises the polyglycerol fatty acid ester in an amount of from 5 to 30 parts by weight, a polyhydric alcohol in an amount of from 5 to 30 parts by weight, an oily component in an amount of from 40 to 90 parts by weight, and water in an amount of from 0.1 to 20 parts by weight.

3. The composition for cosmetics according to claim 1 or 2, wherein said polyglycerol fatty acid ester has an HLB of from 6 to 12.

4. The composition for cosmetics according to claim 1, wherein said composition for cosmetics has a lamellar liquid crystal structure.

5. Cosmetics comprising the composition for cosmetics as defined in claim 1.

6. The cosmetics according to claim 5, wherein the cosmetics are cleansing cosmetics.

7. The composition for cosmetics according to claim 2, wherein said polyglycerol fatty acid ester is polyglyceryl dimyristate, said polyhydric alcohol is maltitol, and said oily component is octyl palmitate.

8. The composition for cosmetics according to claim 7, wherein said polyglyceryl dimyristate has an HLB of from 6 to 12.

9. The composition for cosmetics according to claim 7, having a lamellar liquid crystal structure.

* * * * *